(12) United States Patent
Johannison et al.

(10) Patent No.: US 12,239,778 B2
(45) Date of Patent: Mar. 4, 2025

(54) CANISTER FOR A MOBILE NEGATIVE PRESSURE WOUND THERAPY DEVICE

(71) Applicant: Mölnlycke Health Care AB, Gothenburg (SE)

(72) Inventors: Ulf Johannison, Landvetter (SE); Niclas Flach, Alingsås (SE); Fredrik Sahle, Lindome (SE)

(73) Assignee: Mölnlycke Health Care AB, Mölndal (SE)

( * ) Notice: Subject to any disclaimer, the term of this patent is extended or adjusted under 35 U.S.C. 154(b) by 106 days.

(21) Appl. No.: 17/299,395

(22) PCT Filed: Dec. 12, 2019

(86) PCT No.: PCT/EP2019/084823
§ 371 (c)(1),
(2) Date: Jun. 3, 2021

(87) PCT Pub. No.: WO2020/120657
PCT Pub. Date: Jun. 18, 2020

(65) Prior Publication Data
US 2022/0047800 A1 Feb. 17, 2022

(30) Foreign Application Priority Data
Dec. 14, 2018 (EP) .................... 18212746

(51) Int. Cl.
*A61M 1/00* (2006.01)

(52) U.S. Cl.
CPC .............. *A61M 1/784* (2021.05); *A61M 1/88* (2021.05); *A61M 1/962* (2021.05); *A61M 1/964* (2021.05);
(Continued)

(58) Field of Classification Search
CPC .... A61M 1/98–984; A61M 2205/7536; A61M 1/71; A61M 1/77;
(Continued)

(56) References Cited

U.S. PATENT DOCUMENTS 5,386,735 A * 2/1995 Langdon ................. A61M 1/68
73/864.34
8,414,519 B2 * 4/2013 Hudspeth .............. A61M 1/742
604/313
(Continued)

FOREIGN PATENT DOCUMENTS

DE 102016115836 3/2018
WO WO-2009019496 A2 * 2/2009 .......... A61M 1/0005
(Continued)

OTHER PUBLICATIONS

Zohuriaan-Mehr, Jalal et al. Superabsorbent Polymer Materials: A Review. Iranian Polymer Journal, vol. 17, No. 6, 2008, pp. 451-477 [online], [retrieved on Nov. 16, 2022]. Retrieved from the Internet <URL: https://www.researchgate.net/publication/242582443_Superabsorbent_Polymer_Materials_A_Review> (Year: 2008).*
(Continued)

*Primary Examiner* — Philip R Wiest
*Assistant Examiner* — Linnae E. Raymond
(74) *Attorney, Agent, or Firm* — Ballard Spahr LLP (57) ABSTRACT

Disclosed is a canister for a mobile negative pressure wound therapy (NPWT) device, specifically adapted for ensuring prolonged uninterrupted use of the NPWT device. The canister has an inlet port and a filter member. The canister also includes a bypass member adapted to at least partly allow passage of air from the inlet port to the filter member. Also disclosed is a corresponding NPWT device that includes the canister.

18 Claims, 7 Drawing Sheets

(52) U.S. Cl.
CPC .............. *A61M 1/98* (2021.05); *A61M 1/985* (2021.05); *A61M 1/882* (2021.05); *A61M 2205/8206* (2013.01)

(58) Field of Classification Search
CPC ...... A61M 1/60–631; A61M 1/64–684; A61M 1/88–884; A61M 1/90–985
See application file for complete search history.

(56) References Cited

U.S. PATENT DOCUMENTS

| | | | | |
|---|---|---|---|---|
| 9,931,448 | B2* | 4/2018 | Locke | A61M 1/913 |
| 10,881,324 | B2 | 1/2021 | Ryu et al. | |
| 2013/0053797 | A1* | 2/2013 | Locke | A61M 1/966 |
| | | | | 604/319 |
| 2013/0304004 | A1* | 11/2013 | Riesinger | A61M 1/95 |
| | | | | 604/319 |
| 2014/0276492 | A1 | 9/2014 | Pratt et al. | |
| 2015/0065967 | A1* | 3/2015 | Bendele | A61M 1/60 |
| | | | | 604/319 |
| 2016/0175500 | A1* | 6/2016 | Cali | A61F 13/00042 |
| | | | | 604/319 |
| 2016/0375183 | A1* | 12/2016 | Chen | A61M 1/88 |
| | | | | 128/848 |
| 2017/0165405 | A1 | 6/2017 | Muser et al. | |
| 2017/0281424 | A1 | 10/2017 | Fink et al. | |

FOREIGN PATENT DOCUMENTS

| | | | |
|---|---|---|---|
| WO | WO2016/129816 | 8/2016 | |
| WO | WO 2017/007724 | 1/2017 | |
| WO | WO 2018/036691 | 3/2018 | |
| WO | WO-2018036691 A1 * | 3/2018 | ............ A61M 1/604 |
| WO | WO-2019097288 A1 * | 5/2019 | .......... A61M 1/0001 |

OTHER PUBLICATIONS

"Bypass." Encyclopedia.com [online], [retrieved on Feb. 31, 2024]. Retrieved from the Internet <URL: https://www.encyclopedia.com/medicine/divisions-diagnostics-and-procedures/medicine/bypass> (Year: 2018).*

"Oval shape—meaning, properties, construction, examples." CueMath [online], [retrieved on Nov. 16, 2022]. Retrieved from the Internet <URL: https://www.cuemath.com/geometry/oval-shape/> (Year: 2021).*

International Search Report and Written Opinion were mailed on Feb. 18, 2020 by the International Searching Authority for International Application No. PCT/EP2019/084823, filed on Dec. 12, 2019 and published as WO 2020/120657 on Jun. 18, 2020 (Applicant—Mölnlycke Health Care Ab) (10 Pages).

* cited by examiner

CANISTER FOR A MOBILE NEGATIVE PRESSURE WOUND THERAPY DEVICE

CROSS-REFERENCE TO RELATED APPLICATIONS

This application is a U.S. National Phase Application of International Application No. PCT/EP2019/084823, filed Dec. 12, 2019, which claims priority to European Application No. 18212746.4, filed Dec. 14, 2018, each of which are hereby incorporated by reference in their entirety.

TECHNICAL FIELD

The present disclosure generally relates to a canister for a mobile negative pressure wound therapy (NPWT) device, specifically adapted for ensuring prolonged uninterrupted use of the NPWT device. The present disclosure also relates to a corresponding NPWT device.

BACKGROUND

Negative pressure wound therapy (NPWT) is a technique that promotes healing of e.g. surgical, acute and chronic wounds by the application of a sub-atmospheric pressure to the wound, using a negative pressure pump. The NPWT technique also permits less outside disturbance of the wound as well as for transportation of excess fluids away from the wound site. Generally, the NPWT technique has until now mainly been applied to a patient while in a hospital environment. However, recent product development now allows the technique to be used by a patient in a home environment.

An exemplary implementation of an NPWT device for use in such a home environment is presented in US20170165405, addressing issues in relation to portability and ease of the patient operation the device. Specifically, US20170165405 discloses the use of a removable canister, where the canister can be replaced with another canister, such as when the canister has been filled with a liquid from the wound site. In US20170165405, the canister is arranged to include one or more feet for placing the canister on a surface. The feet(s) can be formed out of rubber, silicone, or any other suitable material and can be angled at a suitable angle so that the canister remains stable when placed on the surface.

Further attention is drawn to WO2017007724, presenting apparatuses for multi-orientation fluid management are described. In some example embodiments, an apparatus for managing fluids may comprise an absorbent core and one or more layers of a fluid acquisition and manifolding material. The fluid acquisition and manifolding material can provide a shell or envelope for capturing the fluid and distributing it to the absorbent core for storage. The manifolding material can distribute fluid as the absorbent core swells.

In US20170281424 there is disclosed a portable system for subatmospheric pressure therapy in connection with healing a surgical wound, includes a wound dressing dimensioned for positioning relative to a wound bed of a subject, a portable subatmospheric pressure mechanism dimensioned to be carried or worn by the subject and a container for collecting exudates from the wound bed removed under the subatmospheric pressure supplied by the subatmospheric pressure mechanism.

Also, in WO2018036691 there is shown a device for providing vacuum for the vacuum treatment of wounds on the human body, comprising a vacuum-producing apparatus and a disposable container that can be disposed of after use, for holding liquids, in particular wound secretions suctioned from a wound.

Even though the above disclosed prior art presents interesting approaches to NPWT devices for use in said home environment and is defined as "mobile", the NPWT devices presented in e.g. US20170165405 is not suitable to be e.g. carried around by patient. That is, the type of NPWT device presented in e.g. US20170165405, WO2017007724, US20170281424, are not considered suitable for placement on its side or upside down, since such an arrangement may result in said liquid entering the negative pressure pump.

Accordingly, there seems to be room for further improvements in how to implement the NPWT device, making it truly mobile, for example allowing the NPWT device to be carried around by the patient.

SUMMARY

In view of above-mentioned and other drawbacks of the prior art, it is an object of the present disclosure to provide improvements in relation to the structural implementation of an NPWT device, ensuring prolonged and undisturbed use of the NPWT device.

According to an aspect of the present disclosure, it is therefore provided a canister for a mobile negative pressure wound therapy (NPWT) device associated with a user, the canister adapted to be in fluid communication with a wound site and capable of receiving fluids from the wound site, wherein the canister comprises an inlet port fluidly coupled to an inner volume of the canister at a first position, an outlet port fluidly coupled to the inner volume of the canister at a second position, the second position being arranged at a preset distance from the first position, a filter member arranged in a vicinity of the outlet port, and a liquid absorbent material arranged inside a portion of the inner volume of the canister, the liquid absorbent material adapted to collect a liquid from the wound site, wherein the canister further comprises a bypass member adapted to at least partly allow passage of air from the inlet port to the filter member.

The inlet of the canister is adapted to be in fluid communication with a wound site of a user/patient (e.g. fluidly connected to wound cover or wound dressing arranged at said wound site), wherein the outlet of the canister is adapted to be fluidly connected to a negative pressure pump.

The filter member is capable of separating liquid and air, that is, the filter member is configured to be substantially gas-permeable and liquid impermeable, provided for ensuring that substantially no liquid is transported out from the canister and into a fluidly connected negative pressure pump. The filter member is preferably arranged inside of the canister and may for example be provided as a membrane allowing substantially only air/gases to pass though the filter member and subsequently be transported through the outlet of the canister.

However, the functionality of the filter member may in some situations, depending on the material used for the filter member, be reduced in case the filter member comes in contact with the liquid, such as in an embodiment where the filter member is arranged to at least partly comprise a hydrophobic membrane. That is, the gas-permeability of the filter may be significantly impaired if the filter member is "wetted", i.e. comes into contact with a liquid, such as the liquid from the wound site, thereby substantially blocking an air communication between the inner volume of the canister and the outlet.

The present disclosure is based upon the realization that the introduction of a liquid absorbent material inside a portion of the inner volume of the canister may be used for "fixating" a liquid from the wound site. By such an implementation, movement of the liquid from the wound site that is collected in the canister is reduced, such that prematurely wetting and thus blocking of the filter member can be avoided or at least reduced. This was according to prior-art solutions often the case when the mobile negative pressure wound therapy (NPWT) device was carried around by the user (e.g. used in multiple orientations). In some embodiments, the liquid absorbent material may be arranged within a portion of the canister defined as collection chamber.

Whereas the liquid absorbent material at an initial stage of operation of the mobile NPWT device may allow air to "flow" there-through, once the liquid absorbent material starts to absorb the liquid from the wound site the throughput of air will be greatly reduced. That is, in case the transportation of air is stopped (or almost stopped); the NPWT device may not deliver the sub-atmospheric pressure to the wound site by means of the above-mentioned negative pressure pump.

Accordingly, in line with the present disclosure the canister is further provided with a bypass member, where the bypass member is specifically adapted to allow air to "flow freely" from the inlet port to the filter member of the canister, even in the situation when the liquid absorbent material is (almost) fully saturated with the liquid from the wound site.

It should be understood that the expressions "negative pressure", "sub-atmospheric pressure", "reduced pressure", as used interchangeably herein, generally refer to a pressure less than a local ambient pressure, such as the ambient pressure in a local environment external to a sealed therapeutic environment provided by a wound cover or dressing. In many cases, the local ambient pressure may also be the atmospheric pressure at which a patient is located. Unless otherwise indicated, values of pressure stated herein are gauge pressures. Similarly, references to increases in negative pressure typically refer to a decrease in absolute pressure, while decreases in negative pressure typically refer to an increase in absolute pressure.

The expression "the second position being arranged at a preset distance from the first position" should within the context of the present disclosure be understood to mean that the inlet and the outlet are typically not positioned directly adjacent to each other. Possibly, the preset distance may for example be 1-5 cm, or dependent on the overall size of the canister.

For ease of understanding of the following discussion of the present disclosure, it should be understood that the expressions "fluidly connect" and "in fluid communication" should be interpreted broadly and may comprise e.g. any form of tubing, conduits, or channels providing a fluid connection/communication, e.g. from the inlet port to the filter member.

The implementation of the canister according to the present disclosure may accordingly allow for a prolonged uninterrupted usage and overall improved mobility of the NPWT device, which is accomplished by means of the inclusion of the liquid absorbent material in combination with the bypass member.

In an embodiment of the present disclosure, the liquid absorbent material is spaced apart from the filter member, such that a space is formed there-between, and the bypass member is arranged to fluidly connect the inlet port with the space between the filter member and the liquid absorbent material. This space may be formed in different ways and depending on the implementation at hand. For example, in a possible embodiment of the present disclosure, the space, e.g. being an empty space, is provided by shaping the liquid absorbent material. That is, the shape of the liquid absorbent material may be configured to include the space. For example, the shape of the liquid absorbent material may be configured (given a specific shape and volume of the canister) such that when the liquid absorbent material is arranged in the canister, the space between the filter member and liquid absorbent material is provided. As such, the liquid absorbent material may for example be hollowed at the side facing the filter member.

As an alternative (or also), the canister may further comprise a spacer arranged between the liquid absorbent material and the filter member, thereby "forcing" the liquid absorbent material away from the filter member. The spacer may in one possible embodiment be arranged to at least partly enclosing the space formed between the filter member and the liquid absorbent material. Providing a separate element (e.g. the spacer) for forcing the liquid absorbent material away from the filter member may in some implementation be advantageous, since such an implementation may ensure that the liquid absorbent material is separated from the filter member also when the liquid absorbent material is partly or fully saturated with the liquid from the wound site, where the liquid absorbent material in some embodiments may expand when saturated.

Preferably, the spacer comprises a plurality of separated "finger portions". By separating the finger portions, with e.g. one or a couple of millimeters, it may be possible to advantageously allow air to "pass between" the fingers even in case the liquid absorbent material has been saturated at the areas where the liquid absorbent material faces the space between the liquid absorbent material and the filter member.

As an alternative, the spacer may be formed by arranging e.g. a net or any other type of partly permeable structure at a distance from the filter member, to ensuring that the liquid absorbent material is adequately spaced apart from the filter member to reduce the risk of wetting of the filter member. One possible type of spacer may for example be a "cap" formed over the filter member, where the cap is provided with a plurality of, in comparison, small openings.

In line with the present disclosure, the canister may preferably comprise a top portion and a bottom portion, and the inlet port and the outlet port are arranged at the top portion of the canister. In a preferred embodiment, the spacer encircles the outlet port and extends a predetermined distance from the outlet port in a direction from the top portion towards the bottom portion of the canister. That is, the liquid absorbent material will be ensured to be forced away from the filter member with the predetermined distance, wherein the predetermined distance may preferably be adapted such that liquid absorbent material does not come in contact with the filter member but at the same time minimizing the open volume (with no liquid absorbent material) where liquid can "flow around". In some embodiments, the predetermined distance may be at least 5 mm, preferably at least 8 mm such as at least 10 mm. The space formed between the liquid absorbent material and the filter member may in some embodiment have a height of at least 5 mm, preferably at least 8 mm such as at least 10 mm. Other predetermined distances (range of predetermined distances) are of course possible and within the scope of the present disclosure. In particular, the predetermined distance may typically be adapted based on a given design of the spacer and/or size of filter member (e.g. extension area).

In an embodiment of the present disclosure, the canister further comprises a filter chamber fluidly connected to the outlet port, wherein the filter member covers a portion of the filter chamber. Such an implementation may advantageously allow for the filter member to have an in comparison "large area", as compared to an implementation where the filter member is solely arranged to cover the outlet port. As such, the filter chamber may be allowed to extend at the top portion of the canister, with a filter area possibly covering more than 25%, preferably more than 50%, of the corresponding area of the top portion of the canister. The arrangement of the filter chamber and the filter member will be further elaborated below in the detailed description.

Preferably, the bypass member is formed as a portion of a wall of the canister, for example formed as a recess in the wall (e.g. the bottom portion) of the canister. Such a recess may advantageously be formed when manufacturing the canister, e.g. by molding the canister in a plastic material. The recess may in some embodiments be at least partly concavely shaped, with curved or right-angled corners (e.g. essentially 90 degrees). However, other shapes are possible and within the scope of the present disclosure. For example, in some embodiments a height of walls of the recess (e.g. a depth of the recess) is selected to be greater than a width of the recess. Possibly the height/depth may be twice the width of the recess. Such exemplary profiles of the recess may in some implementations reduce the risk of the liquid absorbent material to enter into the recess.

Furthermore, in some embodiment the shape of the recess may be arranged such that width of the recess is smaller at the side facing the liquid absorbent material, as compared to the width of the recess at the side of the recess facing away from the liquid absorbent material, as will be illustrated below. That is, it may in some embodiments be desirable to arrange walls of the recess to lean towards each other, such that the "leaning angle" of the walls of the recess is less than 90 degrees (less than right angled).

As an alternative, or also, the bypass member may be provided as a tubular element, possibly "open" along a portion of a longitudinal extension of the tubular element. For example, the tubular element may comprise a plurality of openings or perforations along its extension. Alternatively (or additionally), the tubular element may be made from a porous material, preferably made from a porous gas-permeable and liquid-impermeable material. The element may for example be allowed to pass through or around the liquid absorbent material. By means of allowing the bypass member to be at least partly open towards the liquid absorbent material, it is possible to allow air within or passing through the liquid absorbent material to enter the bypass member, for further flow towards the outlet port of the canister, and/or to allow any liquid that may be present in the bypass to be absorbed by the adjacent liquid absorbent material.

In embodiments of the present disclosure, the liquid absorbent material may comprise an absorbent material selected from the group consisting of polymeric foam, such as a hydrophilic polyurethane foam, a non-woven material, fibrous material such as fibrous hydrophilic polymeric material, gel forming fibers or particles, hydrogel, a matrix containing hydrocolloids, woven and knitted fibers, or any combination thereof. Thereby, the liquid absorbent material is capable of absorbing a liquid (e.g. exudate from a wound).

In embodiments of the present disclosure, the liquid absorbent material may comprise a layer of hydrophilic polyurethane foam material. For example, the hydrophilic foam may be an open-cell porous foam such a hydrophilic polyurethane foam. The foam may for example be a polyurethane foam produced from a composition comprising a prepolymer based on: hexamethylene diisocyanate (HDI), toluene diisocyanate (TDI), or methylene diphenyl diisocyanate (MDI).

As such, the liquid absorbent material may for example be arranged as a hydrophilic sheet, possibly folded within the canister. The hydrophilic sheet is preferably provided as a single sheet of material, where e.g. the single sheet of material has been cut or punched in a predetermined manner such that the sheet of material when folded matches a predetermined portion of the inner volume of the canister.

Alternatively (or also), the liquid absorbent material may be formed as a single component, possibly having a hollowed portion as mentioned above for allowing the liquid absorbent material to be spaced apart from the filter member.

In some embodiments of the present disclosure it may furthermore be desirable to arrange a tongue portion of the liquid absorbent material to extend in a direction towards the inlet port and to adapt the tongue portion to be separated from the inlet port with a predetermined distance. The liquid absorbent material may swell as liquid is being absorbed and thus the predetermined separation distance may preferably be adapted such that a distance between the inlet port and the tongue portion can be ensured upon absorption and swelling. The extent of swelling may vary depending on the properties of the liquid absorbent material and the predetermined separation distance may thus preferably be adapted accordingly. In some embodiments the predetermined separation distance is at least 5 mm, preferably at least 8 mm. In some embodiments the predetermined separation distance is selected within a range of 5-20 mm or 5-10 mm. Such an implementation may in some embodiments minimize the risk that liquid absorbed by the tongue portion temporarily block the inlet port such that transportation of exudate and/or air through the inlet port is reduced. This potential temporary blockage problem may for example arise in situation wherein a relatively large amount of exudate is being transported to the canister in a short period of time and if the absorbed exudate is not being transported away from the tongue portion at the inlet port (e.g. spreading within the liquid absorbent material) at same (or faster) rate as new exudate enters through the inlet port.

In embodiments of the present disclosure, the liquid absorbent material may be characterized by a free swell absorptive capacity, corresponding to the maximum absorptive capacity, of at least 3 times its own weight (i.e. 3 grams absorbed liquid per 1 gram of liquid absorbent material), preferably at least 4 times its own weight such as at least 5 times its own weight, and further preferably at least 6 times its own weight, as measured by EN 13726-1:2002. For example, the liquid absorbent material may have a free swell absorptive capacity, corresponding to the maximum absorptive capacity, of from 3 to 25 g/g (gram of absorbed liquid per gram of liquid absorbent material), as measured by EN 13726-1:2002.

For ease of understanding of the following discussion of the present disclosure, it should be understood that the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

In regard to materials, the term "hydrophilic" generally refers to the water-permeability property of a material or the water-attracting property of a material. In the context of a material with pores (such as, for example, open-cell foams) or materials with through-holes, such a material is typically considered "hydrophilic" if the material wicks up water.

As used herein, the term "open-cell" refers to the pore structure of a foam material, wherein the pores in a pore structure are connected to each other and form an interconnected network with pathways for fluid flow through the foam material.

In embodiments of the present disclosure, the liquid absorbent material may be an open-cell porous hydrophilic foam having a density of 60 to 180 kg/m$^3$ as measured according to standard method ISO 845:2006.

As used herein, the term "layer" or "sheet" should be understood to have a continuous extension in one plane (x and y direction) and a thickness perpendicular to said plane (z direction).

In a possible embodiment of the present disclosure, the canister further comprises a baffle arranged inside the canister between the inlet port and the filter member. The baffle may for example extend from the top portion of the canister towards the bottom of the canister. A possible length of the baffle is between 1-3 cm but may of course depend on the overall size of the canister, possibly extending essentially all the way to the bottom of the canister. The baffle may in some embodiments advantageously be used to protect the filter member by ensuring that the fluid from the wound site is directed towards the liquid absorbent material, thereby further reducing the risk of prematurely wetting and thus blocking the filter member.

Preferably, an inner volume of the canister is between 50-300 ml, preferably configured to collect at least 25 ml of the liquid component of the fluid from the wound site. It may of course be possible to allow the canister to have different inner volumes, for example depending on the type of wound. In a possible embodiment at least 75% of the inner volume of the canister is occupied with the liquid absorbent material. The higher percentage of liquid absorbent material the more of the inner volume can be filled, thereby minimizing open volume where liquid can flow around but at the same time maximizing collection volume without prematurely wetting the filter member, i.e. full capacity of canister can be used while at the same time ensure all collected liquid is locked up by the absorbent.

Furthermore, it is preferred to form the canister of an at least partly transparent or translucent material or to comprise an at least partly transparent portion. By adapting the canister to have at least partly transparent or translucent properties, light (e.g. ambient light) emitted into the canister is allowed to be readily seen by e.g. the user, whereby the user may act in a suitable manner to handle e.g. an issue with the canister. The partly transparent or translucent properties of the canister further allow the user to quickly review a filling status of the canister.

The canister is preferably arranged as a component of the NPWT device, associated with the user. It may generally be preferred that the canister is detachably connected to a housing comprising the negative pressure pump, whereby e.g. a full canister may be removed and replaced with an empty (new) canister. In such an embodiment it may be desirable to provide e.g. the canister and the housing with some form of engagement means for securing the canister to the housing such that the canister is not unintentionally removed from the housing. The engagement means may in one embodiment comprise a pair of flexible protrusions extending from the canister and adapted to engage with e.g. corresponding locking grooves provided at the housing.

According to an alternative aspect of the present disclosure, there is provided a canister for a mobile negative pressure wound therapy (NPWT) device associated with a user, the canister adapted to be in fluid communication with a wound site and capable of receiving fluids from the wound site, wherein the canister comprises an inlet port fluidly coupled to an inner volume of the canister at a first position, an outlet port fluidly coupled to the inner volume of the canister at a second position, the second position being arranged at a preset distance from the first position, a filter member arranged in a vicinity of the outlet port, and a liquid absorbent material arranged inside a portion of the inner volume of the canister, the liquid absorbent material adapted to collect a liquid from the wound site, wherein the liquid absorbent material comprises a foam, and the canister further comprises means for reducing a formation of bubbles within the canister.

In an embodiment where the liquid absorbent material comprises a foam, it may in some embodiments be a risk that the fluids from the wound site (i.e. a combination of air and liquid from the wound site) forms bubbles when mixed and transported through the foam. As a consequence, there is a risk that the bubbles are created from the foam structure and exit the same towards the filter member and thereby wets the filter member (which may cause a blockage of fluid (e.g. air) transport through the filter before the absorption capacity of the canister is fully utilized as discussed above). Accordingly, the means for reducing a formation of bubbles is in line with this aspect of the present disclosure provided for reducing the risk of such bubbles wetting the filter member.

Said means may in some embodiments comprise e.g. the above discussed bypass member, where the bypass member is provided for reducing the amount of air entering the liquid absorbent material provided as a foam, to thereby reducing the formation of bubbles at the foam, by separating air from the liquid being received from the wound site. As an alternative, or also, said means may be provided as a structure arranged to "break" the bubbles before being received at the filter member. Such a structure may for example be provided as a "mesh" or similar, being permeable to air but formed to reduce the risk of any bubbles being received at the filter member.

According to another aspect of the present disclosure, there is further provided a mobile negative pressure wound therapy (NPWT) device associated with a user, comprising a housing, a negative pressure pump arranged within the housing, a canister having an inlet port and an outlet port, wherein the inlet and the outlet port fluidly coupled to an inner volume of the canister, and the outlet port is fluidly connected to the negative pressure pump, wherein the inlet port is adapted to be fluidly connected to a wound cover, the wound cover provided for creating a sealed space defined in part by a wound site, a battery arranged within the housing, the battery provided for powering the NPWT device, and a control unit arranged within the housing, the control unit electrically connected to the battery and adapted to control an operation of the negative pressure pump to selectively establish a negative pressure within the sealed space, wherein the canister comprises a filter member arranged in a vicinity of the outlet port, a liquid absorbent material arranged inside a portion of the inner volume of the canister, the liquid absorbent material adapted to collect a liquid from the wound site, and a bypass member adapted to at least partly allow passage of air from the inlet port to the filter member This aspect of the present disclosure provides similar advantages as discussed above in relation to the previous aspects of the present disclosure.

For ease of understanding of the following discussion of the present disclosure, it should be understood that the expression "wound cover" should be interpreted broadly as any wound site member, e.g. can be a film sealed around periphery of wound site, wherein a wound filler may be used to fill the wound volume prior to the application of such wound cover, and/or wound cover may refer to a backing layer of a wound dressing comprising an additional layer(s) such as for example an absorbent layer.

In an embodiment of the present disclosure, the NPWT device is adapted for home care. Accordingly, in combination with the NPWT device being mobile, the NPWT device may be adapted to be carried by the user, e.g. in a pocket, belt, strap or similar. In addition, for simplifying the (end) user operation of the NPWT device, the NPWT device may additionally be provided with indication means for displaying a symbol providing an indication of an operational status for the NPWT device. In one embodiment the NPWT device may instead of display element be provided with dedicated light sources arranged at an operational front surface of NPWT device for providing the user with the mentioned operational status information.

One form of operational status for the NPWT device may be the filling level of the canister, to be used for indicating to the user when a canister indicated as full is to be changed to a new or an empty canister. For determining the filling status of the canister, the NPWT device may be adapted to comprise at least one pressure sensor arranged in fluid communication with the negative pressure pump. The at least one pressure sensor is advantageously arranged to generate an indication of a current pressure level and to provide the same to the control unit for determining the indication of the filling status.

Advantageously, the NPWT device is provided as a component of a wound treatment system, further comprising the wound cover. This will be further elaborated below in the detailed description of the present disclosure.

Further features of, and advantages with, the present disclosure will become apparent when studying the appended claims and the following description. The skilled addressee realize that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Figure 1:
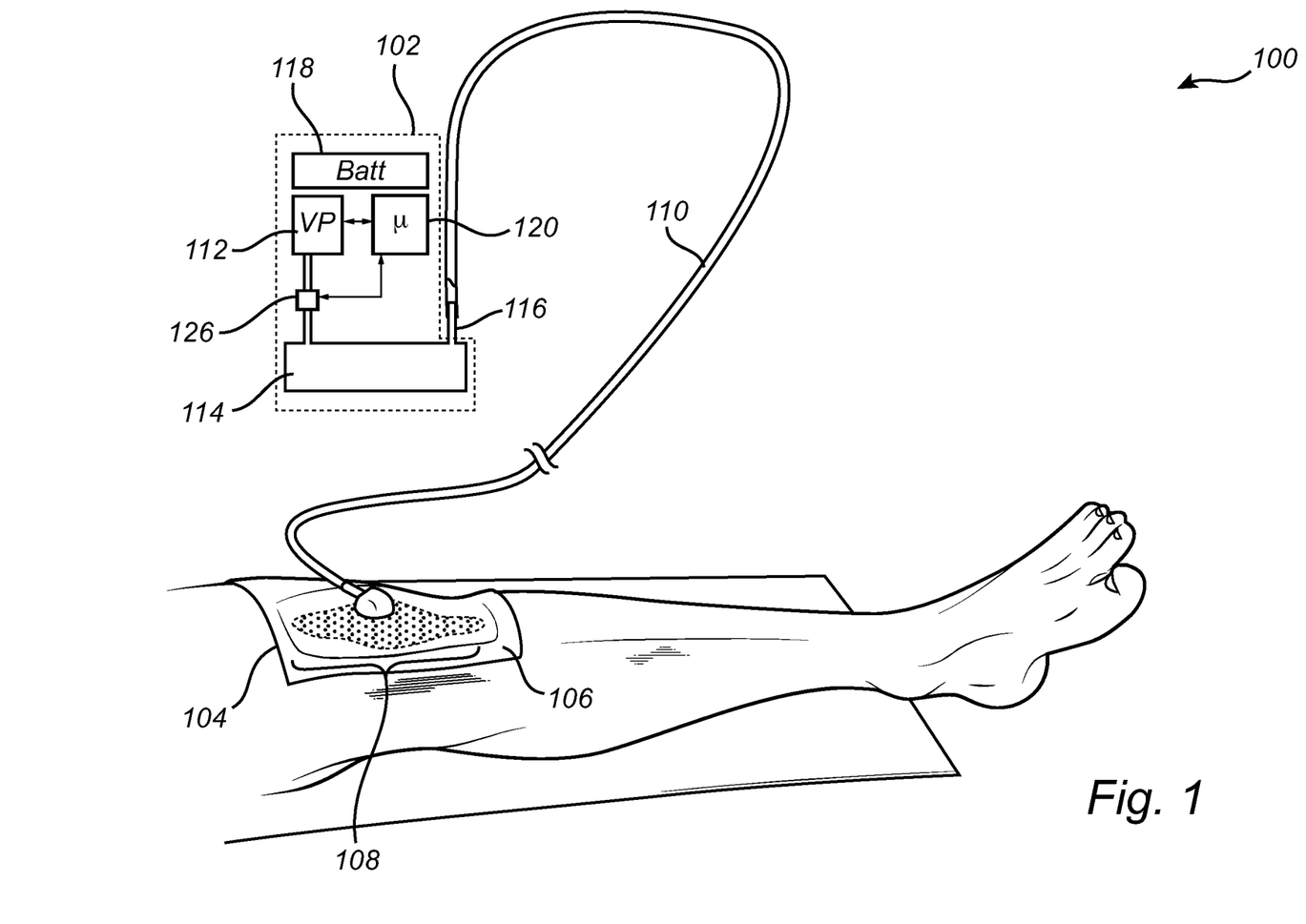
FIG. 1 conceptually illustrates a wound treatment system comprising an NPWT device according to the present disclosure.

Turning now to the drawings and to FIG. 1 in particular, there is conceptually illustrated a wound treatment system 100, comprising a NPWT device 102 in accordance with the present disclosure. The wound treatment system 100 further comprises a wound cover 104, the wound cover 104 being adapted to create a sealed space 106 defined in part by a wound surface 108, such as at the skin of a user/person, at or around a wound of the user/person. Additionally, the NPWT device 102 is fluidly connected to the wound cover 104 using e.g. a tubing 110. The tubing 110 may be of any suitable flexible tubing fabricated from elastomeric and/or polymeric materials.

The NPWT device 102 in turn comprises a negative pressure pump 112 adapted for establishing a negative pressure when the negative pressure pump 112 is in an active state. The negative pressure pump 112 may be any type of pump that is biocompatible and maintains or draws adequate and therapeutic vacuum levels. Preferably, the negative pressure level to be achieved is in a range between about −20 mmHg and about −300 mmHg. In a possible embodiment of the present disclosure, a negative pressure range between about −80 mmHg and about −140 mmHg is used. In a possible embodiment of the present disclosure, the negative pressure pump 112 is a pump of the diaphragmatic or peristaltic type, or the like, in which the moving parts draw the mentioned fluid from the wound cover 104.

The negative pressure pump 112 is fluidly connected to a canister 114, the canister 114 also forming part of the NPWT device 102. The canister 114 may be formed from e.g. molded plastic or the like, and possibly being a detachable component of the NPWT device 102. As mentioned above, the canister 114 is preferably at least partly transparent/translucent to permit viewing into the interior of the canister 114 to assist the user in determining the remaining capacity of the canister 114.

An inlet port 116 is formed at the canister 114, for allowing connection to the tubing 110. The inlet port 116 may also be formed elsewhere at the NPWT device 102, however still fluidly connected to the canister 114. The connection between the inlet port 116 and the tubing 110 is a sealed connection, thus ensuring that no leakage is formed at the inlet port 116 during normal operation of the NPWT device 102. The tubing 110 is preferably releasably connected to the inlet port 116 through conventional means including a friction fit, bayonet coupling, snap fit, barbed connector, or the like. The inlet port 116 may be molded/formed from the same material and/or at the same time as forming the canister 114. A similar sealed connection (e.g. using a flange insulation/"O-ring") is formed between the canister 114 (at the outlet port 310, see e.g. FIG. 3B) and the negative pressure pump 112.

The NPWT device 102 further comprises a battery 118 for powering the NPWT device 102. The battery 118 may preferably be of the rechargeable type but may alternatively be arranged to be disposable and thus to be changed once discharged. A specifically adapted battery pack may be used in relation to some embodiment of the present disclosure.

The NPWT device 102 also comprises a control unit 120, electrically connected to the battery 118 and adapted to control an operation of the negative pressure pump 112. The control unit 120 may include a microprocessor, microcontroller, programmable digital signal processor or another programmable device. The control unit 120 may also, or instead, each include an application specific integrated circuit, a programmable gate array or programmable array logic, a programmable logic device, or a digital signal processor. Where the control unit 120 includes a programmable device such as the microprocessor, microcontroller or programmable digital signal processor mentioned above, the processor may further include computer executable code that controls operation of the programmable device.

In addition, the NPWT device 102 comprises at least one pressure sensor 126 arranged in fluid connection with the negative pressure pump 112.

During use of the NPWT device 102, the wound cover 104 is arranged at a wound site of the user/patient, forming the sealed space 106. The tubing 110 is provided to fluidly connect the wound cover 104 to the inlet port 116 of the NPWT device 102. The NPWT device 102 is then activated, e.g. by the user/patient, by pressing the start/pause button 208 (see FIG. 2A). The negative pressure pump 112 is thereby activated. When activated, the negative pressure pump 112 will start to evacuate air through the canister 114, the inlet port 116, the tubing 110 and the sealed space 106 formed by the wound cover 104. Accordingly, the negative pressure will be created within the sealed space 106. In case a liquid has been formed at the wound site, this liquid from the wound site may at least partly be "drawn" from the wound site, through the tubing 110, the inlet port 116 and into the canister 114. The amount of liquid (possibly defined as exudate) that is drawn from the wound and collected in the canister will depend on the type of wound that is being treated as well as the type of wound dressing used. For example, in case an absorbent dressing is used, the liquid may be absorbed and collected both in the canister and the wound dressing, whereas if a dressing with no or little absorption capacity is used most or all of the liquid from the wound site may be collected in the canister. A suitable filter member (not shown in FIG. 1) is arranged between the canister 114 and the negative pressure pump 112 to ensure that no liquid is allowed to pass to the negative pressure pump 112 from the canister 114.

Figure 2A:
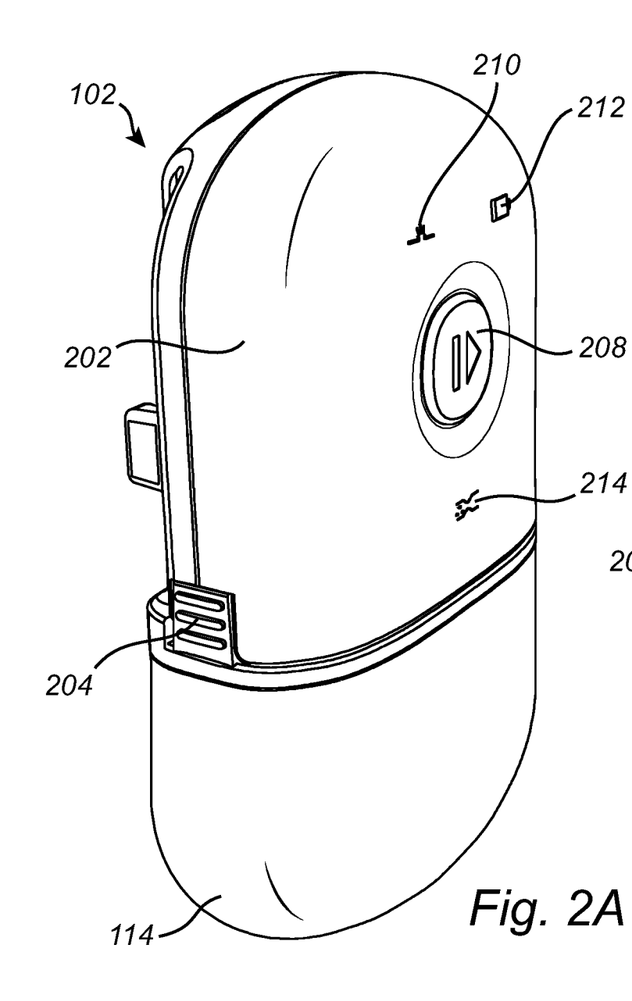
FIGS. 2A and 2B show different views of a possible implementation of the NPWT device shown in FIG. 1.
Figure 2B:
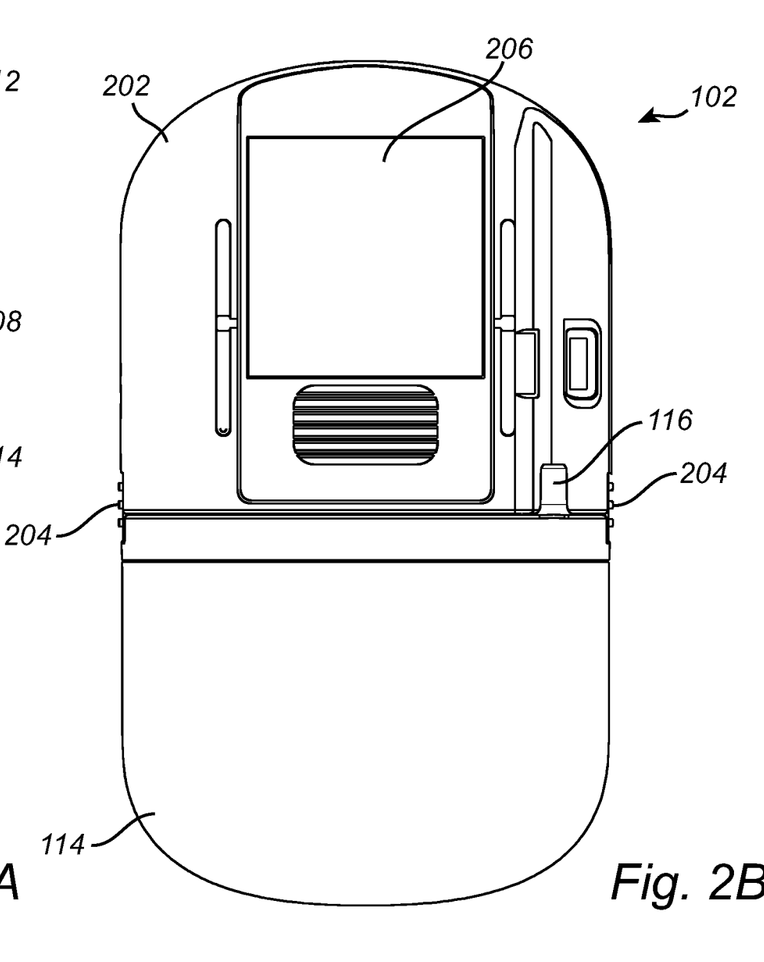

Turning now to FIGS. 2A and 2B illustrating different views of a possible implementation of the NPWT device according to the present disclosure, as shown in FIG. 1. As presented, a majority of the components comprised with the NPWT device 102 are arranged within a housing 202, where the housing 202 may be formed at least partly from plastic.

As presented above, the canister 114 is preferably allowed to be detachably connected to the housing 202. By means of such an implementation it may be possible for the user operating the NPWT device 102 to remove and e.g. discard the canister 114 in case the canister 114 is full or otherwise need to be exchanged (e.g. due to a problem with the canister 114 or the inlet port 116, etc.).

As is shown by the perspective view of FIG. 2A, the canister 114 is provided with a pair of protrusions 204 (one of them shown in FIG. 2A) extending from a top portion of the canister 114. The protrusions 204 may in one embodiment be molded/formed from the same material and/or at the same time as forming the canister 114.

The protrusions 204 are adapted to engage with corresponding locking grooves (not shown) provided at the housing 202, for example allowing a snap fitting between the canister 114 and the housing 202, thereby securing the canister 114 to the housing 202 during normal operation of the NPWT device 102. It should be understood that other means for securing the canister 114 to the housing 202 are possible and within the scope of the present disclosure. In addition, it may in an alternative embodiment be possible to allow the canister 114 to be fixed to or part of the housing 202, thus not detachably connected to the housing 202.

As shown in FIG. 2A, the housing 202 is provided with a start/pause button 208 for initiating/pausing operation of the NPWT device 102. The start/pause button 208 is electrically connected to the control unit 120. In addition, the housing 202 may optionally be provided with one or a plurality of display symbols 210, 212, 214 for providing feedback to the user of the NPWT device 102. For example, the display symbols 210, 212, 214 may provide an indication to the user that there is a possible leakage at e.g. the wound cover 104, that there is a need to charge/change the battery 118, or that there is a blockage in the tubing 110. The display symbols 210, 212, 214 may possible be formed by providing e.g. LEDs below an inner surface of the housing 202, where suitable symbols may be formed, e.g. printed, at an outer surface of the housing 202 at suitable corresponding positions. It should be understood that the display symbols 212, 212, 214 alternatively may be shown on a display screen integrated with the housing 202.

As shown in the back view of FIG. 2B, the canister 114 may be provided with marking allowing the user to visually determining a filling status within the canister 114. In a possible embodiment of the present disclosure the canister has an inner volume of 50-300 ml. In FIG. 2B the inlet port 116 is shown without being connected to the tubing 110.

Additionally, the housing 202 of the NPWT device 102 may comprise a carry clip 206 for allowing the user to e.g. connect the NPWT device 102 to the user's pocket or belt, etc.

Turning now to FIGS. 3A-3D, where detailed illustrations of the canister 114 are provided.

Figure 3A:
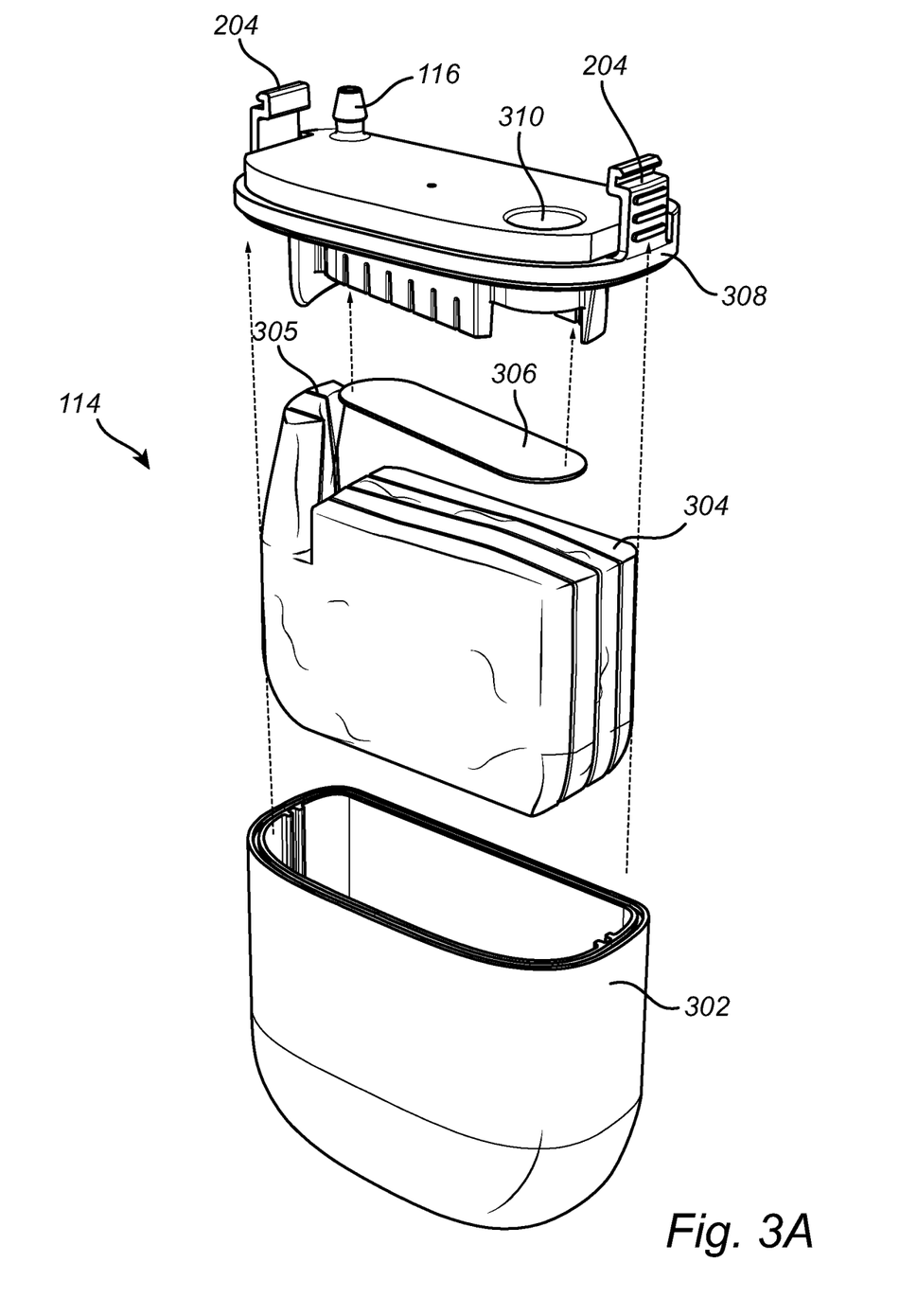
FIGS. 3A-3E provide a detailed presentation of a canister provided in accordance to a currently preferred embodiment of the present disclosure.

FIG. 3A shows an exploded view of the canister 114, where the canister 114 is shown to comprise a bottom portion 302, a liquid absorbent material 304, a filter member 306 and a top portion 308. The top portion 308 in turn comprises the pair of protrusions 204, the inlet port 116 and an outlet port 310. The outlet port 310 is, once connected to the housing 202 of the NPWT device 102 arranged in fluid connection with the negative pressure pump 112.

The bottom portion 302 may be permanently attached to the top portion 308, for example in some embodiments the bottom portion 302 is glued or (plastic) welded together with the top portion 308 of the canister 114.

As is illustrated in FIG. 3A, the liquid absorbent material 304 is presented as a folded sheet member, in a preferred embodiment as a folded hydrophilic sheet. Such a hydrophilic sheet may in some embodiment have a high absorption capacity, such as within the range of 3 to 25 g/g (gram of absorbed liquid per gram of liquid absorbent material), as measured by EN 13726-1:2002. As mentioned above, an inner volume of the canister 114 may be configured to be between 50-300 ml, and as such it is desirable if the canister 114 may be configured to collect at least 50%, more preferably at least 60%, most preferably at least 70%, etc., of the liquid from the wound site within the liquid absorbent material 304. In a possible embodiment at least 75% of the inner volume of the canister is occupied with the liquid absorbent material. The higher percentage of liquid absorbent material the more of the inner volume can be filled, thereby minimizing open volume where liquid can flow around but at the same time maximizing collection volume without prematurely wetting the filter member, i.e. full capacity of canister can be used while at the same time ensure all collected liquid is locked up by the absorbent.

Figure 3B:
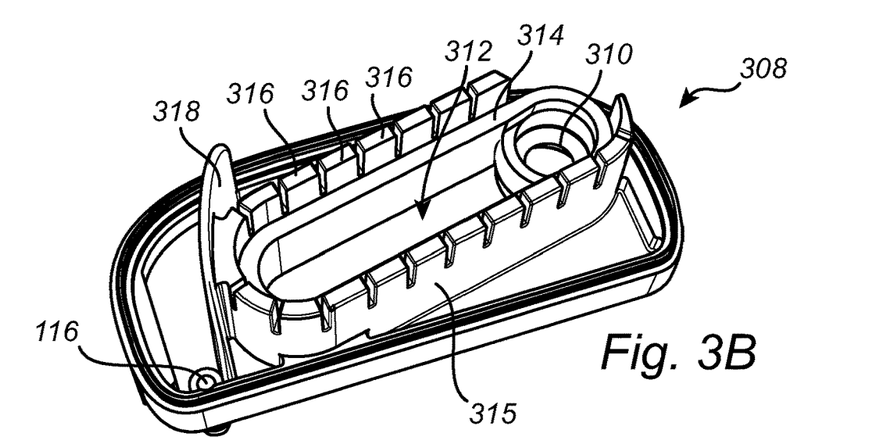

It may in some embodiments be desirable to allow a tongue portion 305 of the liquid absorbent material 304 that is arranged to extend in a direction towards the inlet port 116 (beside a baffle 318 comprised with the top portion 308 as will be further illustrated in FIG. 3B) to have a predetermined separation distance of at least 5 mm, preferably at least 8 mm, from the inlet port 116. For example, the predetermined separation distance may be from 5 to 20 mm or from 5 to 10 mm. The liquid absorbent material 304 may swell as liquid is being absorbed and thus the predetermined separation distance may preferably be adapted such that a distance between the inlet port and the tongue portion can be ensured upon absorption and swelling. The extent of swelling may vary depending on the properties of the liquid absorbent material and the predetermined separation distance may thus preferably be adapted accordingly. Such a predetermined separation distance may in some implementations reduce the risk of a perceived blockage at the inlet port 116. In particular, in case the predetermined separation distance is too small, e.g. if the tongue portion 305 is too close to the inlet port 116, and if a relatively large amount of liquid enters through the inlet port 116 in a short period of time, exudate from the wound that is being absorbed by the tongue portion 305 may not be transported away from area of the inlet port 116 (e.g. spread within the liquid absorbent material) quickly enough and thereby creating a perceived blockage which may also affect (e.g. reduce or block) the transportation of air through the inlet port 116.

In FIG. 3B there is provided a further detailed view of the top portion 308 of the canister 114. FIG. 3B shows inner portions of the inlet port 116 and the outlet port 310. The top portion 308 further comprises a filter chamber 312, where the filter chamber 312 includes an edge 314 to which the filter member 306 is to be fixated (as is further shown in FIG. 3E).

The top portion 308 additionally comprises a spacer 315 constituted of a plurality of fingers 316 slightly spaced apart and extending from the filter chamber 312 towards the liquid absorbent material 304. The fingers 316 are in the illustrated embodiment provided for ensuring that the liquid absorbent material 304 is separated from the filter member 306 with a predetermined distance, such as at least 8 mm. The separation between the liquid absorbent material 304 and the filter member 306 forms a space 317 (see FIG. 3E) there-between, where the space 317 is typically, but not necessarily, an empty space. For example, the space 317 could in some alternative embodiments be filled with e.g. a hydrophobic porous material.

The liquid absorbent material 304 may be press fitted within the bottom portion 302, where the spacer fingers 316 ensures that the desirable space 317 is provided between the liquid absorbent material 304 and the filter member 306.

The top portion 308 of the canister 114 also comprises the above-mentioned baffle 318 arranged between the filter chamber 312 and the inlet port 116. The baffle 318 may in some embodiments advantageously be used to protect the filter member 306 by ensuring that the fluid from the wound site is directed towards the liquid absorbent material 304, thereby further reducing the risk of prematurely wetting and thus at least partly blocking the filter member 306.

As is shown in FIG. 3A an overall area of the filter chamber 312 and thus the filter member 306 is adapted to be larger than the outlet port 310. Accordingly, in case a portion of the filter member 306 would be contacted with the liquid from the wound site such that its function is reduced (i.e. reduced air transportation there through), there is still a chance that some other portion of the filter member 306 is still functionally intact. In FIG. 3A the filter member 306 is shown to be slightly oval, however it should be understood that any shape/form for the filter member 306 is possible and within the scope of the present disclosure.

Figure 3C:
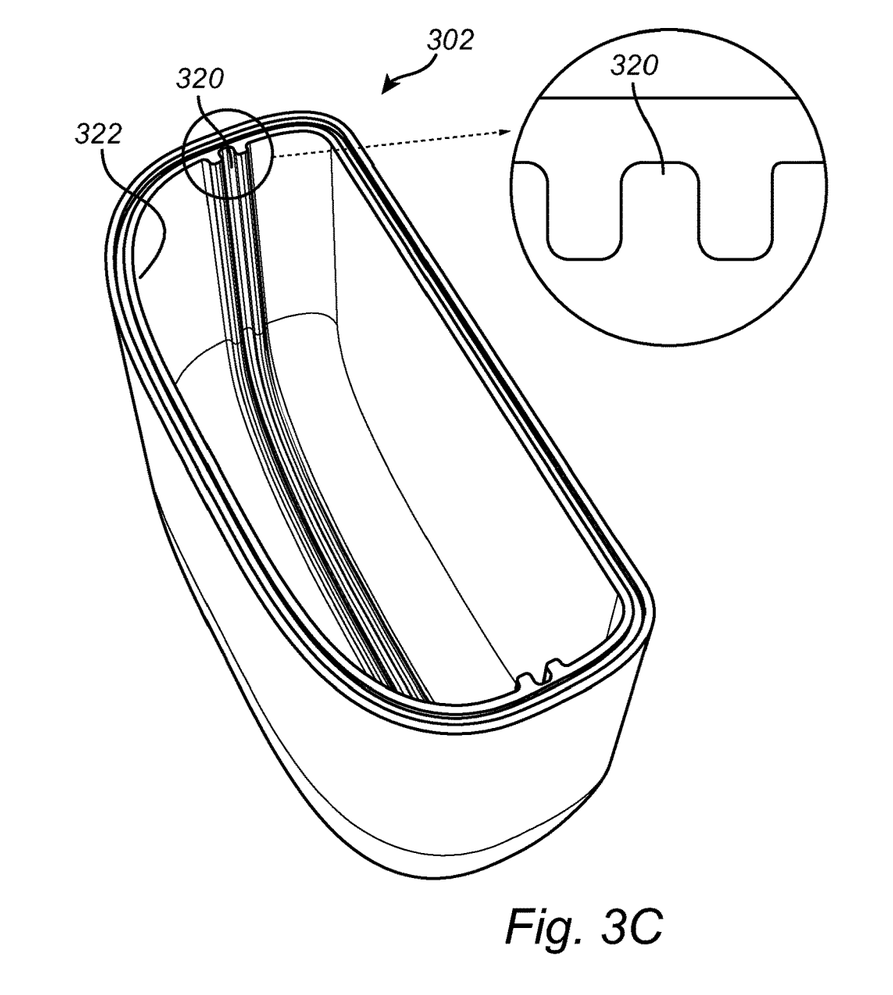

In FIG. 3C there is shown a detailed illustration of the bottom portion 302. Specifically, in the illustration the bottom portion 302 is presented to comprise a bypass member 320 specifically adapted to facilitate transport of air from the inlet port 116 to the filter member 306 of the canister, even in the situation when the liquid absorbent material is (almost) fully saturated with the liquid from the wound site. The bypass member 320 may for example be implemented as illustrated in FIG. 3C, by means of a recess formed within a wall 322 of the bottom portion 302 of the canister 114. In accordance to a desirable implementation of the bypass member 320 as a recess within the wall 322 of the canister 114, the recess is preferably arranged with sharp corners, preferably with corners being with 90 degrees. Such an implementation of the bypass member will reduce the risk of the liquid from the wound site to "get stuck" within the recess of the bypass member 320, or for the liquid absorbent material to enter into the recess, which would reduce the transportation of air therethrough.

Figure 3D:
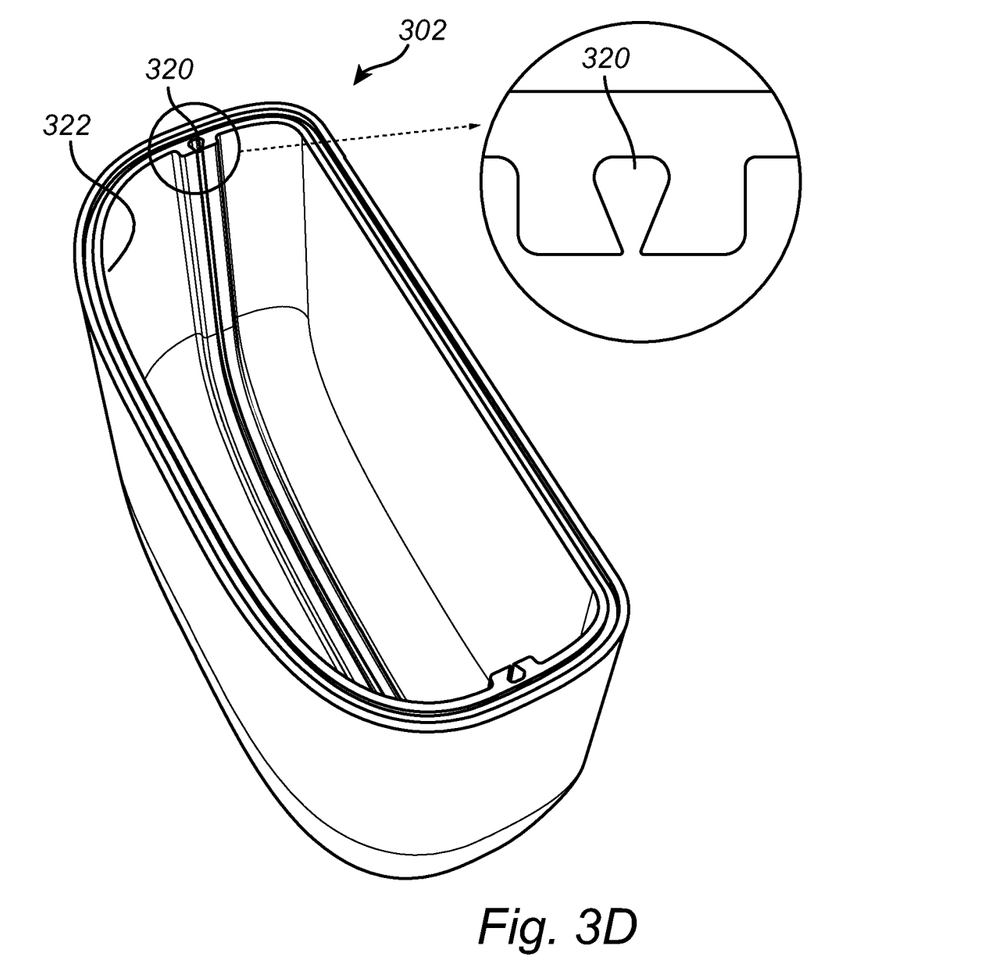

The recess may in some embodiments be at least partly concavely shaped. However, other shapes are possible and within the scope of the present disclosure. For example, and as shown in FIG. 3D, in some embodiment the shape of the recess 320 may be arranged such that width of the recess is smaller at the side facing the liquid absorbent material, as compared to the width of the recess at the side of the recess facing away from the liquid absorbent material. Furthermore, in some embodiments a height of walls of the recess (e.g. a depth of the recess) is selected to be greater than a width of the recess. Possibly the height/depth may be twice the width of the recess. Such exemplary profiles of the recess may in some implementations reduce the risk of the liquid absorbent material to enter into the recess.

Figure 3E:
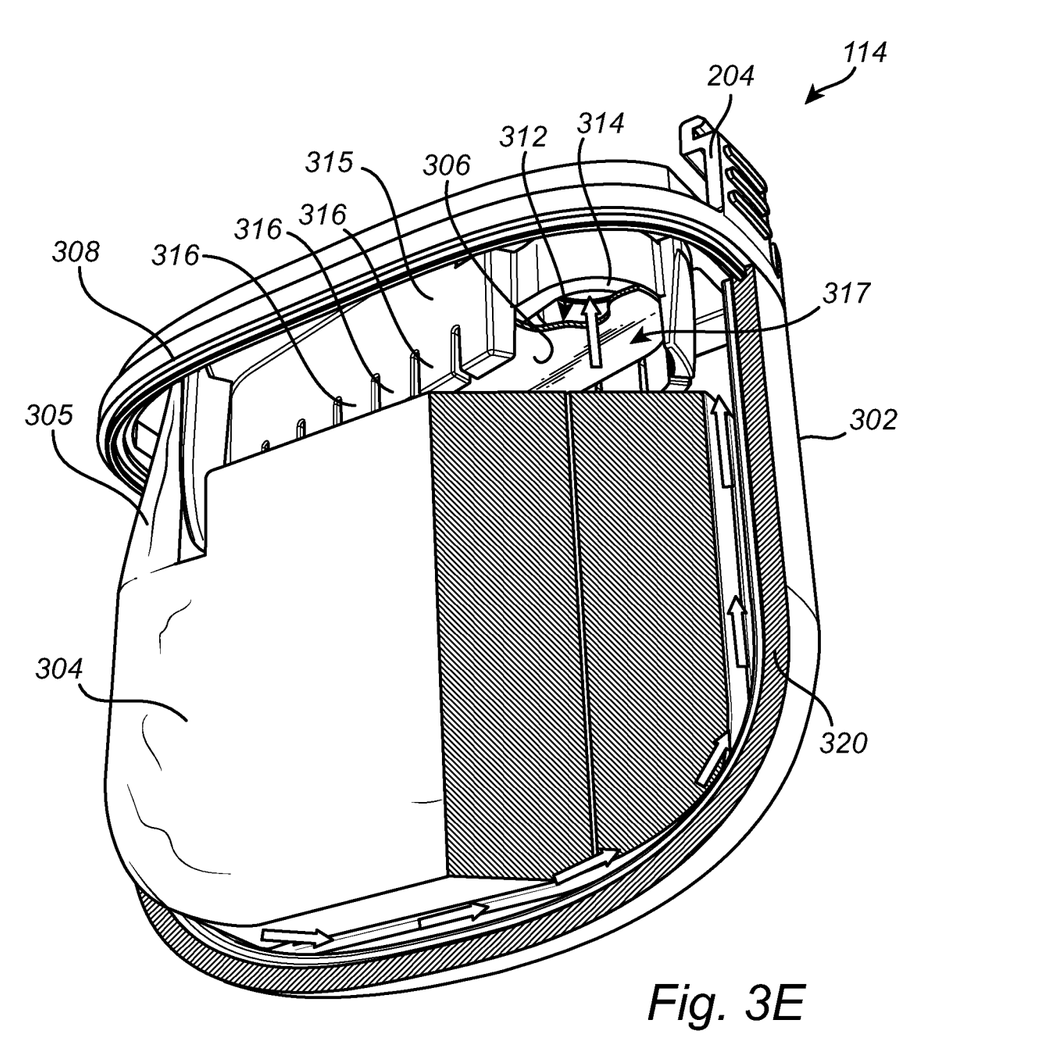

In FIG. 3E there is shown a cross section of the canister 114. As is shown, the filter member 306 has been fixed to the edge 314 of the filter chamber 312. The fixation of the filter member 306 to the edge 314 may for example be by means of a suitable glue of by welding the filter member 306 to the edge 314.

In line with the above discussion provided in regards to use of the NPWT device 102, once the negative pressure pump 112 is activated the fluid from the wound site of the patient will enter through the inlet port 116. The baffle 318 will ensure that the liquid component of the fluid is directed to the liquid absorbent material 304 rather than directly to the filter member 306. The liquid absorbent material 304 will absorb the liquid from the wound site. Air will on the other hand be allowed to pass from the inlet port 116 to the filter member 306 (as shown with the indicative arrows) by means of the bypass member 320, through the outlet port 310 and towards the negative pressure pump 112.

Figure 4A:
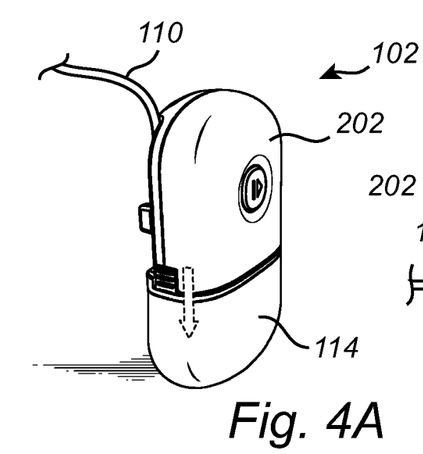
FIGS. 4A-4D present different possible orientations of the NPWT device during its general use.
Figure 4B:
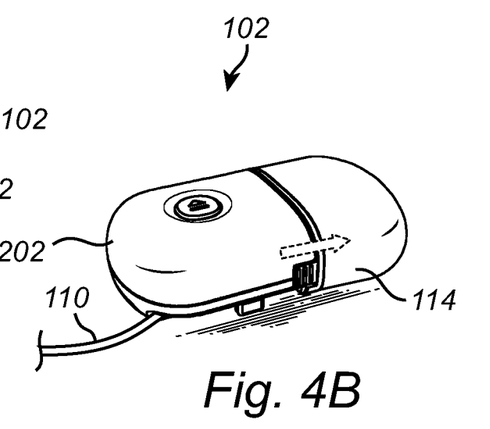
Figure 4C:
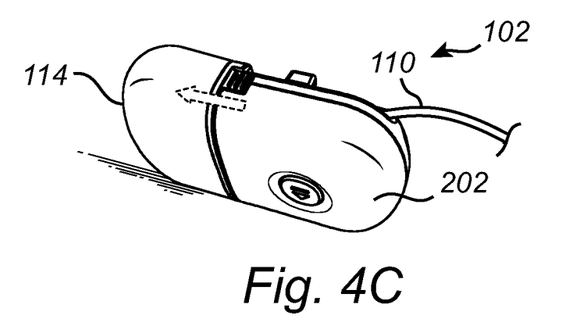
Figure 4D:
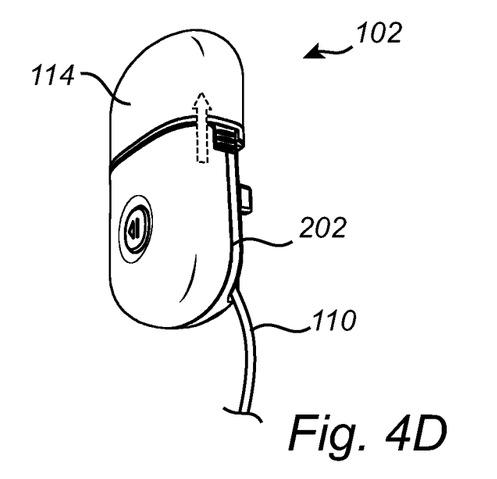

With further reference to FIGS. 4A-4D, there are illustrated four typical positions of the NPWT device 102 during general use. During truly mobile use of the NPWT device 102 the NPWT device 102 may for example be arranged with the canister facing downwards (as shown in FIG. 4A), on the side (as is shown in FIGS. 4B and 4C) or upside down (as sis shown in FIG. 4D).

In all situations (i.e. FIGS. 4A-4D), and in line with the present disclosure, the combination of the liquid absorbent material 304 and the bypass member 320 will ensure that the filter member 306 stays "dry" (and thus functionally intact) for an extended time period and preferably up until the point where the maximum amount of the liquid from the wound site has been received by the liquid absorbent material 304 and thus the canister 114 is to be exchanged to a new/not full canister 114.

In summary, the present disclosure generally relates to a canister 114 for a mobile negative pressure wound therapy (NPWT) device 102, specifically adapted for ensuring prolonged uninterrupted use of the NPWT device.

The present disclosure is based upon the realization that the introduction of the liquid absorbent material inside a portion of the inner volume of the canister may be used for "fixating" a liquid from the wound site, the liquid typically received from a specifically adapted wound dressing/cover fluidly connected to the inlet port of the canister. By such an implementation, the movement of liquid from the wound site as collected in the canister is reduced such that prematurely wetting, and thus blocking, of the filter member can be avoided or at least reduced, which in prior-art solutions often was the case when the mobile negative pressure wound therapy (NPWT) device was carried around by a user.

Accordingly, in line with the concept according to the present disclosure the canister is further provided with e.g. a bypass member, where the bypass member is specifically adapted to allow air to "flow freely" from the input to the filter member of the canister, thereby ensuring prolonged uninterrupted use of the NPWT device.

Although the figures may show a sequence the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps. Additionally, even though the present disclosure has been described with reference to specific exemplifying embodiments thereof, many different alterations, modifications and the like will become apparent for those skilled in the art.

In addition, variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A canister for a mobile negative pressure wound therapy (NPWT) device associated with a user, the canister adapted to be in fluid communication with a wound site and capable of receiving fluids from the wound site, wherein the canister comprises: —an inner wall partially defining an inner volume of the canister, the inner wall having an inner surface, —an inlet port fluidly coupled to the inner volume of the canister at a first position, —an outlet port fluidly coupled to the inner volume of the canister at a second position, the second position being arranged at a preset distance from the first position, —a filter member arranged in a vicinity of the outlet port, and —a liquid absorbent material arranged inside a portion of the inner volume of the canister, the liquid absorbent material adapted to collect a liquid from the wound site, wherein: —the canister further comprises a bypass member adapted to at least partly allow passage of air from the inlet port to the filter member, wherein the bypass member has a length and defines a channel formed as a recess in the inner surface of the inner wall, wherein the channel is in fluid communication with the liquid absorbent material along the entire length of the bypass member, wherein the inner wall comprises a peripheral sidewall portion and a bottom wall portion, wherein the bypass member extends along the peripheral sidewall portion and the bottom wall portion.

2. The canister according to claim 1, wherein the liquid absorbent material is spaced apart from the filter member such that a space is formed there-between, and the bypass member is arranged to fluidly connect the inlet port with the space between the filter member and the liquid absorbent material.

3. The canister according to claim 2, wherein the canister further comprises a spacer arranged between the liquid absorbent material and the filter member.

4. The canister according to claim 3, wherein the spacer at least partly encloses the space formed between the filter member and the liquid absorbent material.

5. The canister according to claim 3, wherein the spacer comprises a plurality of separated finger portions.

6. The canister according to claim 3, wherein the canister comprises a top portion and a bottom portion, and the spacer encircles the outlet port and extends a predetermined distance from the filter member in a direction from the top portion towards the bottom portion of the canister.

7. The canister according to claim 1, further comprising a filter chamber fluidly connected to the outlet port, wherein the filter member covers a portion of the filter chamber.

8. The canister according to claim 7, wherein the filter chamber has an oval shape.

9. The canister according to claim 1, wherein the liquid absorbent material comprises a hydrophilic polyurethane foam or a hydrophilic sheet.

10. The canister according to claim 1, wherein the inner volume of the canister is between 50-300 ml.

11. The canister according to claim 1, wherein a tongue portion of the liquid absorbent material is arranged to extend in a direction towards the inlet port and is adapted to be separated from the inlet port with a predetermined separation distance.

12. The canister according to claim 11, wherein the predetermined distance is selected within a range of 5-20 mm.

13. A mobile negative pressure wound therapy (NPWT) device associated with a user, wherein the NPWT device comprises a canister according to claim 1.

14. The NPWT device according to claim 13, wherein the canister is detachably connected to a housing.

15. The canister according to claim 1, wherein the bypass member comprises a first portion that extends along the bottom wall portion, wherein the first portion of the bypass member has opposite ends, wherein the bypass member further comprises a second and a third portion that extend upwardly from respective opposite ends of the first portion of the bypass member.

16. A canister for a mobile negative pressure wound therapy (NPWT) device associated with a user, the canister adapted to be in fluid communication with a wound site and capable of receiving fluids from the wound site, wherein the canister comprises: —an inner wall partially defining an inner volume of the canister, the inner wall having an inner surface, —an inlet port fluidly coupled to the inner volume of the canister at a first position, —an outlet port fluidly coupled to the inner volume of the canister at a second position, the second position being arranged at a preset distance from the first position, —a filter member arranged in a vicinity of the outlet port, —a liquid absorbent material arranged inside a portion of the inner volume of the canister, the liquid absorbent material adapted to collect a liquid from the wound site, and —a baffle arranged between the inlet port and the liquid absorbent material, wherein: —the canister further comprises a bypass member adapted to at least partly allow passage of air from the inlet port to the filter member, wherein the bypass member has a length and defines a channel formed as a recess in the inner surface of the inner wall, wherein the channel is in fluid communication with the liquid absorbent material along the length of the bypass member, wherein the inner wall comprises a peripheral sidewall portion and a bottom wall portion, wherein the bypass member extends along the peripheral sidewall portion and the bottom wall portion.

17. A mobile negative pressure wound therapy (NPWT) device associated with a user, comprising: —a housing, —a negative pressure pump arranged within the housing, —a canister having an inlet port and an outlet port, wherein the inlet and the outlet port are fluidly coupled to an inner volume of the canister, and the outlet port is fluidly connected to the negative pressure pump, wherein the inlet port is adapted to be fluidly connected to a wound cover, the wound cover provided for creating a sealed space defined in part by a wound site, —a battery arranged within the housing, the battery provided for powering the NPWT device, and —a control unit arranged within the housing, the control unit electrically connected to the battery and adapted to control an operation of the negative pressure pump to selectively establish a negative pressure within the sealed space, wherein the canister comprises: —an inner wall partially defining the inner volume of the canister, the inner wall having an inner surface, —a filter member arranged in a vicinity of the outlet port, —a liquid absorbent material arranged inside a portion of the inner volume of the canister, the liquid absorbent material adapted to collect a liquid from the wound site, and —a bypass member adapted to at least partly allow passage of air from the inlet port to the filter member, wherein the bypass member has a length and defines a channel formed as a recess in the inner surface of the inner wall, wherein the channel is in fluid communication with the liquid absorbent material along the entire length of the bypass member, wherein the inner wall comprises a peripheral sidewall portion and a bottom wall portion, wherein the bypass member extends along the peripheral sidewall portion and the bottom wall portion.

18. A wound treatment system, comprising:
an NPWT device according to claim 17, and
a wound cover.

\* \* \* \* \*